(12) United States Patent
Sherwood

(10) Patent No.: US 11,262,354 B2
(45) Date of Patent: Mar. 1, 2022

(54) DISPOSABLE SENSOR ELEMENTS, SYSTEMS, AND RELATED METHODS

(71) Applicant: CARDIAC PACEMAKERS, INC., St. Paul, MN (US)

(72) Inventor: Gregory J. Sherwood, North Oaks, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 460 days.

(21) Appl. No.: 14/883,895

(22) Filed: Oct. 15, 2015

(65) Prior Publication Data

US 2016/0109440 A1  Apr. 21, 2016

Related U.S. Application Data

(60) Provisional application No. 62/065,951, filed on Oct. 20, 2014.

(51) Int. Cl.
*G01N 33/543* (2006.01)
*G01N 27/22* (2006.01)
*G01N 33/497* (2006.01)

(52) U.S. Cl.
CPC ..... *G01N 33/54366* (2013.01); *G01N 27/227* (2013.01); *G01N 33/497* (2013.01)

(58) Field of Classification Search
CPC ........... G01N 33/54366; G01N 27/227; G01N 33/497
USPC ................. 600/532, 529, 543; 73/23.3, 23.2; 422/84, 98; 204/403.01, 403.02, 403.03
See application file for complete search history.

(56) References Cited

U.S. PATENT DOCUMENTS

| | | | |
|---|---|---|---|
| 3,661,528 | A | 5/1972 | Falk |
| 3,952,730 | A | 4/1976 | Key |
| 3,981,297 | A | 9/1976 | Dunn et al. |
| 4,901,727 | A | 2/1990 | Goodwin |

(Continued)

FOREIGN PATENT DOCUMENTS

| | | |
|---|---|---|
| CN | 102183557 | 9/2011 |
| CN | 102941042 | 2/2013 |

(Continued)

OTHER PUBLICATIONS

Groves et al. Analysis of Solvent Vapors in Breath and Ambient Air with a Surface Acoustic Wave Sensor Array, 2001, Annals of Occupational Hygiene, vol. 45, No. 8, pp. 609-623. (Year: 2001).*

(Continued)

*Primary Examiner* — Melanie Brown
(74) *Attorney, Agent, or Firm* — Pauly, DeVries Smith & Deffner LLC

(57) ABSTRACT

Embodiments include disposable sensor elements, systems including the same and related methods. In an embodiment, a disposable sensor element is included having a substrate and a first measurement zone comprising a plurality of discrete binding detectors. The first measurement zone can define a portion of a first gas flow path. In some embodiments the disposable sensor element can further include a second measurement zone, separate from the first measurement zone. The second measurement zone can include a plurality of discrete binding detectors. The second measurement zone can be disposed outside of the first gas flow path. Other embodiments are also included herein.

19 Claims, 6 Drawing Sheets

(56) References Cited

U.S. PATENT DOCUMENTS

| | | |
|---|---|---|
| 5,174,290 A | 12/1992 | Fiddian-Green |
| 5,186,172 A | 2/1993 | Fiddian-Green |
| 5,357,971 A | 10/1994 | Sheehan et al. |
| 5,423,320 A | 6/1995 | Salzman et al. |
| 5,704,368 A | 1/1998 | Asano et al. |
| 5,834,626 A | 11/1998 | De Castro et al. |
| 5,928,155 A | 7/1999 | Eggers et al. |
| 6,006,121 A | 12/1999 | Vantrappen et al. |
| 6,029,076 A | 2/2000 | Fiddian-Greene et al. |
| 6,085,576 A * | 7/2000 | Sunshine ............ G01N 33/0031 340/634 |
| 6,149,624 A | 11/2000 | Mcshane |
| 6,192,168 B1 * | 2/2001 | Feldstein ............ G01N 21/552 385/12 |
| 6,238,339 B1 | 5/2001 | Fiddian-Greene et al. |
| 6,248,078 B1 | 6/2001 | Risby et al. |
| 6,312,390 B1 | 11/2001 | Phillips et al. |
| 6,480,734 B1 | 11/2002 | Zhang et al. |
| 6,599,253 B1 | 7/2003 | Baum et al. |
| 6,615,066 B2 | 9/2003 | Huyberechts et al. |
| 6,712,770 B2 | 3/2004 | Lin et al. |
| 6,726,637 B2 | 4/2004 | Phillips et al. |
| 6,733,464 B2 | 5/2004 | Olbrich et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,972,277 B2 | 7/2011 | Oki et al. |
| 7,988,917 B2 | 8/2011 | Roesicke et al. |
| 7,992,422 B2 | 8/2011 | Leddy et al. |
| 8,043,860 B2 | 10/2011 | Leznoff et al. |
| 8,052,933 B2 | 11/2011 | Schirmer et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,244,355 B2 | 8/2012 | Bennett et al. |
| 8,366,630 B2 | 2/2013 | Haick et al. |
| 8,479,731 B2 | 7/2013 | Heinonen et al. |
| 8,481,324 B2 | 7/2013 | Nakhoul et al. |
| 8,494,606 B2 | 7/2013 | Debreczeny et al. |
| 8,529,459 B2 | 9/2013 | Stahl, Jr. et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,955,367 B2 | 2/2015 | Gouma et al. |
| 9,011,779 B1 | 4/2015 | Jensen et al. |
| 9,029,168 B2 | 5/2015 | Mannoor et al. |
| 9,103,775 B2 | 8/2015 | Bradley et al. |
| 9,147,398 B2 | 9/2015 | White et al. |
| 9,147,851 B1 | 9/2015 | Bartsch et al. |
| 9,299,238 B1 | 3/2016 | Ahmad et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Jensen et al. |
| 9,513,244 B2 | 12/2016 | Koester |
| 9,528,979 B2 | 12/2016 | Haick et al. |
| 9,618,476 B2 | 4/2017 | Goldsmith |
| 9,642,577 B1 | 5/2017 | Li et al. |
| 9,696,311 B2 | 7/2017 | Haick et al. |
| 9,763,600 B2 | 9/2017 | Van Kesteren et al. |
| 9,765,395 B2 | 9/2017 | Goldsmith |
| 9,936,897 B2 | 4/2018 | Carlson et al. |
| 9,977,011 B2 | 5/2018 | Beck et al. |
| 10,034,621 B2 | 7/2018 | Wondka et al. |
| 10,046,323 B2 | 8/2018 | Bos |
| 10,307,080 B2 | 6/2019 | Ssenyange et al. |
| 10,770,182 B2 | 9/2020 | Sherwood et al. |
| 10,852,264 B2 | 12/2020 | Kelly et al. |
| 2002/0123749 A1 | 9/2002 | Jain et al. |
| 2002/0142477 A1 * | 10/2002 | Lewis ................ G01N 33/0031 436/151 |
| 2003/0051733 A1 | 3/2003 | Kotmel et al. |
| 2004/0039295 A1 | 2/2004 | Olbrich et al. |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2007/0265509 A1 | 11/2007 | Burch et al. |
| 2008/0021339 A1 | 1/2008 | Gabriel et al. |
| 2008/0038154 A1 | 2/2008 | Longbottom et al. |
| 2008/0146890 A1 | 6/2008 | Leboeuf et al. |
| 2008/0161709 A1 | 7/2008 | Bradley |
| 2008/0183910 A1 | 7/2008 | Natoli et al. |
| 2008/0228098 A1 | 9/2008 | Popov et al. |
| 2008/0317636 A1 | 12/2008 | Brahim et al. |
| 2009/0054799 A1 | 2/2009 | Vrtis et al. |
| 2009/0112115 A1 | 4/2009 | Huang et al. |
| 2010/0024533 A1 | 2/2010 | Kimura et al. |
| 2010/0056892 A1 | 3/2010 | Ben-Barak et al. |
| 2010/0085067 A1 | 4/2010 | Gabriel et al. |
| 2010/0137733 A1 | 6/2010 | Wang et al. |
| 2010/0147303 A1 | 6/2010 | Jafari et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0143962 A1 | 6/2011 | Chaubron et al. |
| 2011/0201956 A1 | 8/2011 | Alferness et al. |
| 2011/0269632 A1 | 11/2011 | Haick et al. |
| 2011/0283770 A1 | 11/2011 | Hok et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | McCracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 * | 4/2013 | Schentag ............ G01N 21/17 435/25 |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |

(56) References Cited

U.S. PATENT DOCUMENTS

| | | | |
|---|---|---|---|
| 2014/0145735 A1 | 5/2014 | Koester et al. | |
| 2014/0171817 A1 | 6/2014 | Blanch et al. | |
| 2014/0194703 A1 | 7/2014 | Wondka et al. | |
| 2014/0275597 A1 | 9/2014 | Zhang et al. | |
| 2014/0275854 A1 | 9/2014 | Venkatraman et al. | |
| 2014/0276168 A1 | 9/2014 | Vissapragada Venkata Satya et al. | |
| 2014/0294675 A1 | 10/2014 | Melker et al. | |
| 2014/0318535 A1 | 10/2014 | Bullock et al. | |
| 2014/0378790 A1 | 12/2014 | Cohen | |
| 2015/0013429 A1 | 1/2015 | Atkin et al. | |
| 2015/0038378 A1 | 2/2015 | Cheng et al. | |
| 2015/0044710 A1 | 2/2015 | Dasgupta et al. | |
| 2015/0065365 A1 | 3/2015 | Ahmad | |
| 2015/0164373 A1 | 6/2015 | Davis et al. | |
| 2015/0196251 A1 | 7/2015 | Outwater et al. | |
| 2015/0250408 A1* | 9/2015 | Ssenyange | G01N 33/0016 600/532 |
| 2015/0257676 A1 | 9/2015 | Fries | |
| 2015/0265184 A1 | 9/2015 | Wondka et al. | |
| 2015/0295562 A1 | 10/2015 | Agarwal et al. | |
| 2015/0301021 A1 | 10/2015 | Haick et al. | |
| 2015/0307936 A1 | 10/2015 | Goldsmith | |
| 2015/0309018 A1 | 10/2015 | Goldsmith | |
| 2015/0320338 A1 | 11/2015 | Kane et al. | |
| 2015/0335266 A1 | 11/2015 | Cormier | |
| 2015/0335267 A1 | 11/2015 | Cormier et al. | |
| 2015/0338340 A1 | 11/2015 | Jiang et al. | |
| 2015/0338390 A1 | 11/2015 | Anglin et al. | |
| 2015/0351699 A1 | 12/2015 | Addison et al. | |
| 2016/0025675 A1 | 1/2016 | Goldsmith | |
| 2016/0054312 A1 | 2/2016 | Goldsmith | |
| 2016/0089089 A1 | 3/2016 | Kakkar et al. | |
| 2016/0116431 A1 | 4/2016 | Accardi et al. | |
| 2016/0150995 A1 | 6/2016 | Ratto et al. | |
| 2016/0157752 A1 | 6/2016 | Cho et al. | |
| 2016/0192861 A1 | 7/2016 | Gedeon et al. | |
| 2016/0231309 A1 | 8/2016 | Ahmad et al. | |
| 2016/0334381 A1 | 11/2016 | King-smith et al. | |
| 2016/0334386 A1 | 11/2016 | Anglin et al. | |
| 2016/0370337 A1 | 12/2016 | Blackley | |
| 2017/0014043 A1 | 1/2017 | Mcdonnell | |
| 2017/0042435 A1 | 2/2017 | Vermeulen et al. | |
| 2017/0053068 A1 | 2/2017 | Pillai et al. | |
| 2017/0227491 A1 | 8/2017 | Johnson et al. | |
| 2017/0307562 A1 | 10/2017 | Goldsmith | |
| 2017/0307576 A1 | 10/2017 | Anglin, Jr. et al. | |
| 2017/0360337 A1 | 12/2017 | Sherwood et al. | |
| 2017/0361599 A1 | 12/2017 | Lerner et al. | |
| 2017/0365474 A1 | 12/2017 | Pan et al. | |
| 2017/0365477 A1 | 12/2017 | Pan et al. | |
| 2017/0365562 A1 | 12/2017 | Pan et al. | |
| 2018/0035932 A1 | 2/2018 | Massova | |
| 2018/0037952 A1 | 2/2018 | Goldsmith | |
| 2018/0037985 A1 | 2/2018 | Myers et al. | |
| 2018/0110444 A1 | 4/2018 | Sherwood et al. | |
| 2018/0328841 A1 | 11/2018 | Graham et al. | |
| 2018/0336970 A1 | 11/2018 | Sherwood et al. | |
| 2019/0025237 A1 | 1/2019 | Kelly et al. | |
| 2019/0178837 A1 | 6/2019 | Xu et al. | |
| 2019/0254538 A1 | 8/2019 | Erdman et al. | |
| 2019/0286866 A1 | 9/2019 | Gurt | |
| 2020/0166435 A1 | 5/2020 | Sherwood et al. | |
| 2020/0191737 A1 | 6/2020 | Sherwood et al. | |
| 2021/0148848 A1 | 5/2021 | Kelly et al. | |

FOREIGN PATENT DOCUMENTS

| | | | |
|---|---|---|---|
| CN | 103332678 | 10/2013 | |
| EP | 1764153 | 3/2007 | |
| EP | 1806414 | 7/2007 | |
| EP | 3093653 | 11/2016 | |
| EP | 3431977 | 1/2019 | |
| JP | H11174051 | 7/1999 | |
| JP | 2011102747 | 5/2011 | |
| JP | 2016122249 | 7/2016 | |
| WO | 9947905 | 9/1999 | |
| WO | 2001070114 | 9/2001 | |
| WO | 2008088780 | 7/2008 | |
| WO | 2009135070 | 11/2009 | |
| WO | 2011109736 | 9/2011 | |
| WO | 2012135565 | 10/2012 | |
| WO | 2013095730 | 6/2013 | |
| WO | WO-2013189502 A1 * | 12/2013 | ........ B01L 3/502761 |
| WO | 2014064740 | 5/2014 | |
| WO | 2015191558 | 12/2015 | |
| WO | 2016064740 | 4/2016 | |
| WO | 2016105464 | 6/2016 | |
| WO | 2017218464 | 12/2017 | |
| WO | 2018075731 | 4/2018 | |
| WO | 2018213564 | 11/2018 | |

OTHER PUBLICATIONS

Arasaradnam, R. P. et al., "Review Article: Next Generation Diagnostic Modalities in Gastroenterology—Gas Phase Volatile Compound Biomarker Detection," Alimentary Pharmacology and Therapeutics 2014; 39, pp. 780-789.

Boots, Agnes W. et al., "The Versatile Use of Exhaled Volatile Organic Compounds in Human Health and Disease," J. Breath Res. 6 (2012) 027108, p. 1-21.

Droscher, S. et al., "Quantum Capacitance and Density of States of Graphene," Phys. Scr. T146 (2012) 014009, pp. 1-5.

Ebrish, M. A. et al., "Dielectric Thickness Dependence of Quantum Capacitance in Graphene Varactors with Local Metal Back Gates," Device Research Conference, 2012 (2 pages).

"FDC1004 4-Channel Capacitance-to-Digital Converter for Capacitive Sensing Solutions," Texas Instruments Data Sheet SNOSCY5B, Aug. 2014—Revised 2015 (24 pages).

"FDC1004EVM User Guide," Texas Instruments, Aug. 2014—Revised Oct. 2016 (46 pages).

Fisher, James P. et al., "Central Sympathetic Overactivity: Maladies and Mechanisms," Autonomic Neuroscience 148.1 (2009), pp. 5-15.

Georgakilas, Vasilios et al., "Functionalization of Graphene: Covalent and Non-Covalent Approaches, Derivatives and Applications," Chemical Reviews, Nov. 14, 2012; 112(11), 59 pages.

"International Preliminary Report on Patentability," for PCT Application No. PCT/US2015/056243 dated May 4, 2017 (8 pages).

"International Search Report and Written Opinion," for PCT Application No. PCT/US2017/037144 dated Oct. 6, 2017 (11 pages).

Koester, Steven J. "Using the Quantum Capacitance in Graphene to Enable Varactors for Passive Wireless Sensing Applications," 2011 IEEE Sensors Proceedings, 2011, (4 pages).

Li, Xiao et al., "Digital Health: Tracking Physiomes and Activity Using Wearable Biosensors Reveals Useful Health-Related Information," PLOS Biology, 15.1, (2017), pp. 1-30.

"Mechanical Data," DGS (S-PDSO-G10) DSC0010B Package Outline, Example Board Layout, and Stencil Design, Texas Instruments, 2016, (5 pages).

Nakhleh, Morad K. et al., "Diagnosis and Classification of 17 Diseases from 1404 Subjects via Pattern Analysis of Exhaled Molecules," ACS Nano 2017, 11, pp. 112-125.

"Nano Mobile Healthcare Inc.," Company Profile on Reuters.com URL <http://www.renters.com/finance/stocks/companyProfile?symbol=VNTH.PK> accessed Mar. 17, 2017 (2 pages).

"Package Materials Information," Tape and Reel Information and Box Dimensions. Texas Instruments, Texas Instruments, Feb. 13, 2016, (2 pages).

"Package Option Addendum," Packaging Information, Texas Instruments, May 2015, (2 pages).

"Standard Terms and Conditions for Evaluation Modules," Texas Instruments, 2016, (5 pages).

Wang, David "FDC1004: Basics of Capacitive Sensing and Applications," Application Report SNOA927, Texas Instruments, Dec. 2014, pp. 1-12.

"International Search Report and Written Opinion," for PCT Application No. PCT/US2015/056243, dated Jan. 26, 2016 (12 pages).

(56) References Cited

OTHER PUBLICATIONS

Deen, David A. et al., "Graphene-Based Quantum Capacitance Wireless Vapor Sensors," IEEE Sensors Journal, vol. 14, No. 5, May 2014, pp. 1459-1466.
Georgakilas, Vasilios et al., "Functionalization of Graphene: Covalent and Non-Covalent Approaches, Derivatives and Applications," Chemical Reviews, 2012, 14:112(11), pp. 6156-6214.
Hu, Yuhai et al., "Chemically Functionalized Graphene and Their Applications in Electrochemical Energy Conversion and Storage," Advances in Graphene Science, Chapter 7, 2013, pp. 161-190.
"International Search Report and Written Opinion," for PCT Application No. PCT/US2017/057318 dated Feb. 6, 2018 (14 pages).
Ebrish, M. A. et al., "Operation of Multi-Finger Graphene Quantum Capacitance Varactors using Planarized Local Bottom Gate Electrodes," Applied Physics Letters, A I P Publishing LLC, 2012 (5 pages).
"European Search Report," for Dutch Patent Application No. 2019492 dated Apr. 12, 2018 (10 pages).
Ma, Rui et al., "Acetone Sensing Using Graphene Quantum Capacitance Varactors," 2016 IEEE Sensors, Orlando, FL, 2016 (3 pages).
Oprea, A. et al., "Integrated Temperature, Humidity and Gas Sensors on Flexible Substrates for Low-Power Applications," 007 IEEE Sensors, Atlanta, GA, 2007, pp. 158-161.
International Search Report and Written Opinion for PCT Application No. PCT/US2018/033166 dated Oct. 2, 2018 (12 pages).
Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).
Communication Pursuant to Article 94(3) EPC for European Patent Application No. 18180455.0 dated Feb. 11, 2019 (6 pages).
Deen, David A. et al., "Graphene-Based Quantum Capacitance Wireless Vapor Sensors," IEEE Sensors Journal, vol. 14, No. 5, May 2014 (8 pages).
Ebrish, M.A. et al., "Operation of multi-finger graphene quantum capacitance varactors using planarized local bottom gate electrodes," Applied Physics Letters, vol. 100, No. 14, Apr. 2012 (4 pages).
European Search Report for European Patent Application No. 18180455.0 dated Dec. 3, 2018 (5 pages).
First Office Action for Chinese Patent Application No. 201580056417.2 dated Feb. 11, 2019 (13 pages) with English summary.
International Preliminary Report on Patentability for PCT Application No. PCT/US2017/057318 dated May 2, 2019 (11 pages).
International Preliminary Report on Patentability for PCT Application No. PCT/US2018/037144 dated Dec. 27, 2018 (7 pages).
Ma, Rui et al., "Acetone Sensing Using Graphene Quantum Capacitance Varactors," IEEE Sensors, Oct. 30, 2016 (3 pages).
Opera, A. et al., "Integrated Temperature, Humidity and Gas Sensors on Flexible Substrates for Low-Power Applications," Sensors, Jan. 1, 2007 (4 pages).
Response to Communication Pursuant to Article 94(3) EPC for European Patent Application No. 18180455.0 filed Jun. 6, 2019 (44 pages).
Response to Communication Pursuant to Rules 161 (1) and 162 EPC for European Patent Application No. 17733246.7 filed May 29, 2019 (22 pages).
Non-Final Office Action for U.S. Appl. No. 15/787,985 dated Oct. 10, 2019 (40 pages).
Second Office Action for Chinese Patent Application No. 201580056417.2 dated Sep. 25, 2019 (6 pages) No English Translation.
Communication Pursuant to Article 94(3) EPC for European Patent Application No. 15790739.5 dated Dec. 17, 2019 (5 pages).
Communication Pursuant to Article 94(3) EPC for European Patent Application No. 18180455.0 dated Dec. 20, 2019 (3 pages).
Final Office Action for U.S. Appl. No. 15/787,985 dated Jan. 17, 2020 (16 pages).
International Preliminary Report on Patentability for PCT Application No. PCT/US2018/033166 dated Nov. 28, 2019 (8 pages).
Non-Final Office Action for U.S. Appl. No. 15/982,506 dated Dec. 11, 2019 (41 pages).
Response to Communication Pursuant to Article 94(3) EPC for European Patent Application No. 18180455.0 filed Nov. 12, 2019 (9 pages).
Response to Communication Pursuant to Rules 161(1) and 162 EPC for European Patent Application No. 17794832.0 filed Dec. 6, 2019 (9 pages).
Response to Non-Final Rejection dated Oct. 10, 2019 for U.S. Appl. No. 15/787,985, submitted via EFS-Web on Jan. 7, 2020, 17 pages.
Bhadra, Sharmista et al., "Non-destructive detection of fish spoilage using a wireless basic volatile sensor," Talanta, vol. 134, Dec. 25, 2014 pp. 718-723 (6 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
Final Office Action for U.S. Appl. No. 15/621,103 dated Jun. 8, 2020 (21 pages).
International Search Report and Written Opinion for PCT Application No. PCT/US2019/063324 dated Mar. 27, 2020 (17 pages).
International Search Report and Written Opinion for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Navaneethan, Udayakumar et al., "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).
Non-Final Office Action for U.S. Appl. No. 15/621,103 dated Feb. 21, 2020 (58 pages).
Non-Final Office Action for U.S. Appl. No. 16/037,218 dated Apr. 29, 2020 (46 pages).
Notice of Allowance for U.S. Appl. No. 15/982,506 dated May 7, 2020 (17 pages).
Olson, Eric J. et al., "Capacitive Sensing of Intercalated H2O Molecules Using Graphene," ACS Appl. Mater. Interfaces 2015, 7(46), 25804-25812 (29 pages).
Response to Communication Pursuant to Article 94(3) EPC for European Patent Application No. 15790739.5 filed Apr. 24, 2020 (16 pages).
Response to Communication Pursuant to Article 94(3) EPC for European Patent Application No. 18180455.0 filed Apr. 21, 2020 (24 pages).
Response to Final Rejection dated Jan. 17, 2020 for U.S. Appl. No. 15/787,985, submitted via EFS-Web on Apr. 9, 2020, 12 pages.
Response to Non-Final Rejection dated Dec. 11, 2019 for U.S. Appl. No. 15/982,506, submitted via EFS-Web on Feb. 25, 2020, 13 pages.
Response to Non-Final Rejection dated Feb. 21, 2020 for U.S. Appl. No. 15/621,103, submitted via EFS-Web on May 20, 2020.
Third Office Action for Chinese Patent Application No. 201580056417.2 dated Feb. 18, 2020 (6 pages) No English Translation.
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, SENSORS 2016—Proceedings, Orlando, FL 2016 (3 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
"Non-Final Office Action," for U.S. Appl. No. 15/787,985 dated Apr. 16, 2021 (16 pages).
"Office Action," for Japanese Patent Application No. 2019-520955 dated Feb. 9, 2021 (11 pages) with English Translation.
"Response to Communication Pursuant to Article 94(3) EPC," for European Patent Application No. 18731579.1 filed Mar. 15, 2021 (12 pages).
"Response to Final Rejection," dated Oct. 21, 2020 for U.S. Appl. No. 15/787,985, submitted via EFS-Web on Jan. 21, 2021, 8 pages.

(56) References Cited

OTHER PUBLICATIONS

"Response to Non-Final Rejection," dated Oct. 23, 2020 for U.S. Appl. No. 15/621,103, submitted via EFS-Web on Jan. 22, 2021, 17 pages.
Notice of Allowance for U.S. Appl. No. 16/037,218 dated Jul. 31, 2020 (20 pages).
Office Action for Japanese Patent Application No. 2019-520955 dated Jul. 14, 2020 (5 pages) No English Translation.
Response to Communication Pursuant to Rules 161(1) and 162 EPC for European Patent Application No. 18731579.1 filed Jul. 17, 2020 K19 pages).
Response to Non-Final Rejection dated Apr. 29, 2020 for U.S. Appl. No. 16/037,218, submitted via EFS-Web on Jul. 15, 2020, 7 pages.
Communication Pursuant to Article 94(3) EPC for European Patent Application No. 18731579.1 dated Nov. 10, 2020 (5 pages).
Final Office Action for U.S. Appl. No. 15/787,985 dated Oct. 21, 2020 (21 pages).
First Office Action for Chinese Patent Application No. 201780030595.7 dated Nov. 2, 2020 (12 pages) with English Summary.
Non-Final Office Action for U.S. Appl. No. 15/621,103 dated Oct. 23, 2020 (27 pages).
Office Action for Japanese Patent Application No. 2019-563876 dated Nov. 4, 2020 (3 pages) No English Translation.
Response to Final Rejection dated Jun. 8, 2020 and Advisory Action dated Sep. 4, 2020, for U.S. Appl. No. 15/621,103, submitted via EFS-Web on Oct. 8, 2020, 16 pages.
Response to Final Rejection dated Jun. 8, 2020 for U.S. Appl. No. 15/621,103, submitted via EFS-Web on Aug. 20, 2020, 16 pages.
Response to Non-Final Rejection dated Jun. 29, 2020 for U.S. Appl. No. 15/787,985, submitted via EFS-Web on Sep. 29, 2020, 9 pages.
"Extended European Search Report," for European Patent Application No. 20214733.6 dated Apr. 21, 2021 (11 pages).
"Final Office Action," for U.S. Appl. No. 15/621,103 dated Apr. 22, 2021 (20 pages).
"International Preliminary Report on Patentability," for PCT Application No. PCT/US2019/063324 dated Jun. 10, 2021 (10 pages).
"International Preliminary Report on Patentability," for PCT Application No. PCT/US2019/065981 dated Jul. 1, 2021 (8 pages).
"International Search Report and Written Opinion," for PCT Application No. PCT/US2021/026778 dated Aug. 3, 2021 (11 pages).
"New Summons to Attend Oral Proceedings," for European Patent Application No. 18731579.1 dated Jul. 12, 2021 (6 pages).
"Non-Final Office Action," for U.S. Appl. No. 15/787,985 dated Jun. 29, 2020 (14 pages).
"Notice of Allowance," for U.S. Appl. No. 15/621,103 dated Aug. 3, 2021 (18 pages).
"Notice of Allowance," for U.S. Appl. No. 15/787,985 dated Jul. 15, 2021 (14 pages).
"Office Action," for Chinese Patent Application No. 201780065376.2 dated Apr. 27, 2021 (10 pages) with English Summary.
"Response to Final Rejection," dated Apr. 22, 2021 and the Advisory Action dated Jul. 8, 2021 for U.S. Appl. No. 15/621,103, submitted via EFS-Web on Jul. 12, 2021, 13 pages.
"Response to Final Rejection," dated Apr. 22, 2021 for U.S. Appl. No. 15/621,103, submitted via EFS-Web on Jun. 22, 2021, 13 pages.
"Response to Non-Final Rejection," dated Apr. 16, 2021 for U.S. Appl. No. 15/787,985, submitted via EFS-Web on Jun. 22, 2021, 11 pages.
"Second Office Action," for Chinese Patent Application No. 201780030595.7 dated Jun. 17, 2021 (8 pages), with English Summary.
"Summons to attend oral proceedings pursuant to Rule 115(1) EPC," for European Patent Application No. 18731579.1 dated Jul. 1, 2021 (6 pages).
Chamberlain II, Richard V., et al. "Electrostatically-induced Inclusion of Anions in Cyclodextrin Monolayers on Electrodes," Langmuir 2000, 1388-1396 (9 pages).
Di Natale, Corrado, et al. "Lung Cancer Identification by the Analysis of Breath by Means of an Array of Non-Selective Gas Sensors," Biosensors and Bioelectronics 18 (2003) 1209-1218 (10 pages).
Georgakilas, Vasilios, et al. "Noncovalent Functionalization of Graphene and Graphene Oxide for Energy Materials, Biosensing, Catalytic, and Biomedical Applications," Chern. Rev. 2016, 116, 5464-5519 (56 pages).
Guo, Yujing, et al."Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Machado, Roberto F., et al. "Detection of Lung Cancer by Sensor Array Analyses of Exhaled Breath," Am J RespirCrit Care Med, vol. 171, 1286-1291 (2005), 6 pages.
Planz, B., et al. "The role of urinary cytology for detection of bladder cancer," EJSO (2005) 21, 304-308 (5 pages).
Putta, Chandrababu, et al. "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
Ramakumar, Sanjay, et al. "Comparison of Screening Methods in the Detection of Bladder Cancer," The Journal of Urology vol. 161, 388-394, Feb. 1999 (7 pages).
Rojas, Maria T., et al. "Supported Monolayers Containing Preformed Binding-Sites-Synthesis and Interfacial Binding-Properties of a Thiolated Beta-Cyclodextrin Derivative," J. Am. Chem. Soc. 1995, 117, 336-343 (8 pages).
Wayu, Mulugeta B., et al. "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).
Zhang, Xu, et al. "A Wide Measurement Range and Fast Update Rate Integrated Interface for Capacitive Sensors Array," IEEE Transactions on Circuits and Systems—1: Regular Papers, Vo. 61, No. 1, Jan. 2014, pp. 2-11 (10 pages).

\* cited by examiner

DISPOSABLE SENSOR ELEMENTS, SYSTEMS, AND RELATED METHODS

This application claims the benefit of U.S. Provisional Application No. 62/065,951, filed Oct. 20, 2014, the content of which is herein incorporated by reference in its entirety.

FIELD

Embodiments herein relate to disposable sensor elements, systems including the same, and related methods.

BACKGROUND

The accurate detection of diseases can allow clinicians to provide appropriate therapeutic interventions. Further, the early detection of diseases can lead to better treatment outcomes. Diseases can be detected using many different techniques including analyzing tissue samples, analyzing various bodily fluids, diagnostic scans, and the like.

Some disease states result in the production of specific chemical compounds. As such, the detection of these chemical compounds or patterns of the same can allow for the early detection of particular disease states.

SUMMARY

Embodiments herein include disposable sensor elements, systems including the same and related methods. In some aspects, a disposable sensor element is included. The disposable sensor element can include a substrate, and a first measurement zone comprising a plurality of discrete binding detectors. In some embodiments, the disposable sensor element can also include a second measurement zone, separate from the first measurement zone, comprising a plurality of discrete binding detectors. The first measurement zone can define a portion of a first gas flow path. The second measurement zone can be disposed outside of the first gas flow path.

In addition, in some aspects, the substrate can have a first side and a second side opposite the first side. The first measurement zone and the second measurement zone can both be disposed on the first side. In other aspects, the first measurement zone can be disposed on the first side and the second measurement zone can be disposed on the second side. In some aspects, the second measurement zone of the disposable sensor element can define a portion of a second gas flow path.

In addition, in various aspects a third measurement zone can be included, the third measurement zone can be isolated from the first gas flow path and the second gas flow path.

In addition, in some aspects, the disposable sensor element can further include a component to store reference data.

In addition, in some aspects, the discrete binding detectors can include a passive electrical circuit. In some aspects the electrical properties of the electrical circuit can change upon binding with a component from a gas sample. In addition, in some aspects the discrete binding detectors can include a metal-graphene-oxide capacitor.

In addition, in some aspects, the discrete binding detectors can be functionalized with analyte binding receptors capable of specific binding. In some aspects the analyte binding receptors can include at least one component selected from the group consisting of antibodies, antibody fragments, nonimmuno-proteins, nucleic acids, small molecule receptors, and inorganic receptors.

In addition, in some aspects, a baffle can be mounted on the substrate, the baffle can define a portion of the first gas flow path. In some aspects, a second baffle can also be mounted on the substrate, the baffle can define a portion of a second gas flow path.

In various aspects, the discrete receptor elements are ordered based on the molecular weight of the chemical compound to which they specifically bind. In some aspects, the discrete receptor elements are ordered based on the polarity of the chemical compound to which they specifically bind.

In some aspects, a method of making a disposable sensor element is included. The method can include depositing one or more measurement zones onto a substrate. In some aspects, the method can further include depositing a plurality of discrete binding detectors within the measurement zones on the substrate. In some aspects, the method can include functionalizing the discrete binding detectors with analyte binding receptors capable of specific and/or non-specific analyte binding. The method can further include depositing a component to store reference data onto the substrate. In some aspects, the measurement zones can all be disposed on the same side of the substrate. In other aspects, the measurement zones can be disposed onto different sides of the substrate.

In some aspects, a method of assaying a gas sample is included. The method can include inserting a disposable sensor element into a testing machine. The disposable sensor element can include a substrate and a first measurement zone including a plurality of discrete binding detectors. The first measurement zone can define a portion of a first gas flow path. The disposable sensor element can further include a second measurement zone separate from the first measurement zone. The second measurement zone can include a plurality of discrete binding detectors. The second measurement zone can be disposed outside of the first gas flow path. In some aspects, the method can further include prompting a subject to blow air into the testing machine to follow the first gas flow path. In some aspects, the method can further include interrogating the discrete binding detectors to determine their analyte binding status. In some aspects, the method can further include discarding the disposable sensor element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventor(s) are not entitled to antedate any publication and/or patent, including any publication and/or patent cited herein.

Embodiments herein relate to systems, disposable sensor elements, and related methods for detecting chemical compounds in gas samples, such as the exhaled breath of a patient. By way of example, the systems and disposable sensor elements herein can be used to detect volatile organic compounds and/or patterns of the same that, in turn, can be used to identify disease states such as cancer, cardiac diseases, infections, multiple sclerosis, Alzheimer's disease, Parkinson's disease, and the like. In some embodiments, graphene-based sensors are included on disposable sensor elements that can be used in conjunction with breath analysis systems in order to accurately sense very low concentrations of analytes and/or analyte patterns in order to allow the rapid detection of disease states with high sensitivity. Aspects of some exemplary embodiments will now be described in greater detail with reference to the figures.

Figure 1:
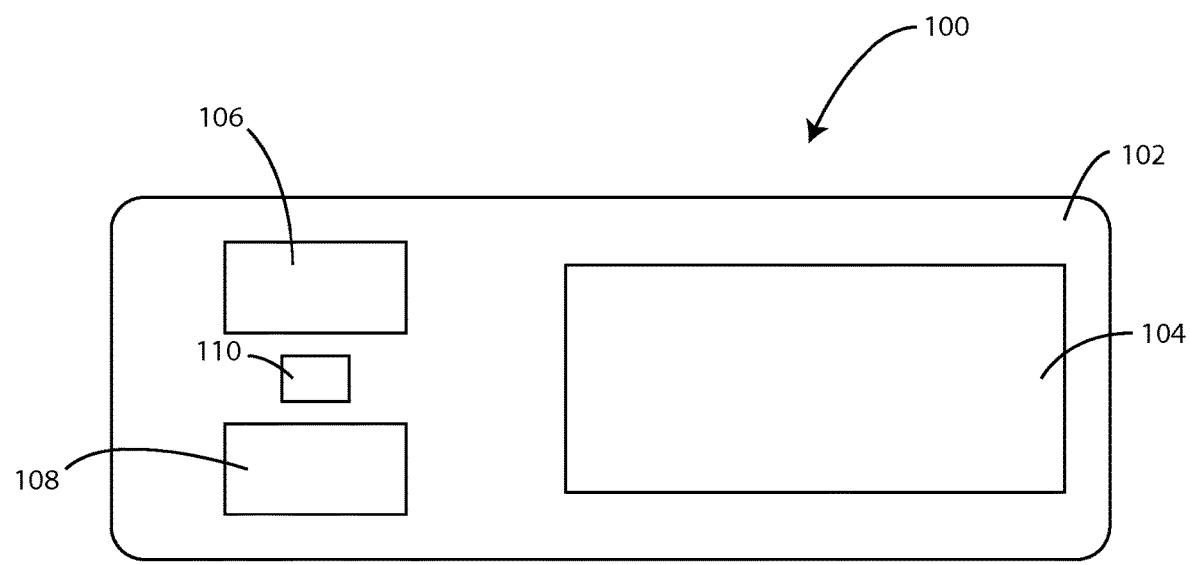
FIG. 1 is a schematic top plan view of a disposable sensor element in accordance with various embodiments herein.

Referring now to FIG. 1, a schematic top plan view of a disposable sensor element 100 is shown in accordance with various embodiments herein. The disposable sensor element 100 can include a substrate 102. It will be appreciated that the substrate can be formed from many different materials. By way of example, the substrate can be formed from polymers, metals, glasses, ceramics, cellulosic materials, composites, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the width (perpendicular to the major axis) can be from about 0.2 cm to about 8 cm.

A first measurement zone 104 can be disposed on the substrate 102. In some embodiments, the first measurement zone 104 can define a portion of a first gas flow path. The first measurement zone (or gas sample zone) 104 can include a plurality of discrete binding detectors. A second measurement zone (or environment sample zone) 106, separate from the first measurement zone 104, can also be disposed on the substrate 102. The second measurement zone 106 can also include a plurality of discrete binding detectors. In some embodiments, the second measurement zone 106 can include the same (in type and/or number) discrete binding detectors that are within the first measurement zone 104. In some embodiments, the second measurement zone 106 can include only a subset of the discrete binding detectors that are within the first measurement zone 104. In operation, the data gathered from the first measurement zone, which can be reflective of the breath sample analyzed, can be corrected or normalized based on the data gathered from the second measurement zone, which can be reflective of analytes present in the environment.

In some embodiments, a third measurement zone (drift control or witness zone) 108 can also be disposed on the substrate. The third measurement zone 108 can include a plurality of discrete binding detectors. In some embodiments, the third measurement zone 108 can include the same (in type and/or number) discrete binding detectors that are within the first measurement zone 104. In some embodiments, the third measurement zone 108 can include only a subset of the discrete binding detectors that are within the first measurement zone 104. In some embodiments, the third measurement zone 108 can include discrete binding detectors that are different than those of the first measurement zone 104 and the second measurement zone 106. Aspects of the third measurement zone are described in greater detail below.

The first measurement zone, the second measurement zone, and the third measurement zone can be the same size or can be of different sizes. The disposable sensor element 100 can also include a component 110 to store reference data. The component 110 to store reference data can be an electronic data storage device, an optical data storage device, a printed data storage device (such as a printed code), or the like. The reference data can include, but is not limited to, data regarding the third measurement zone (described in greater detail below).

Figure 2:
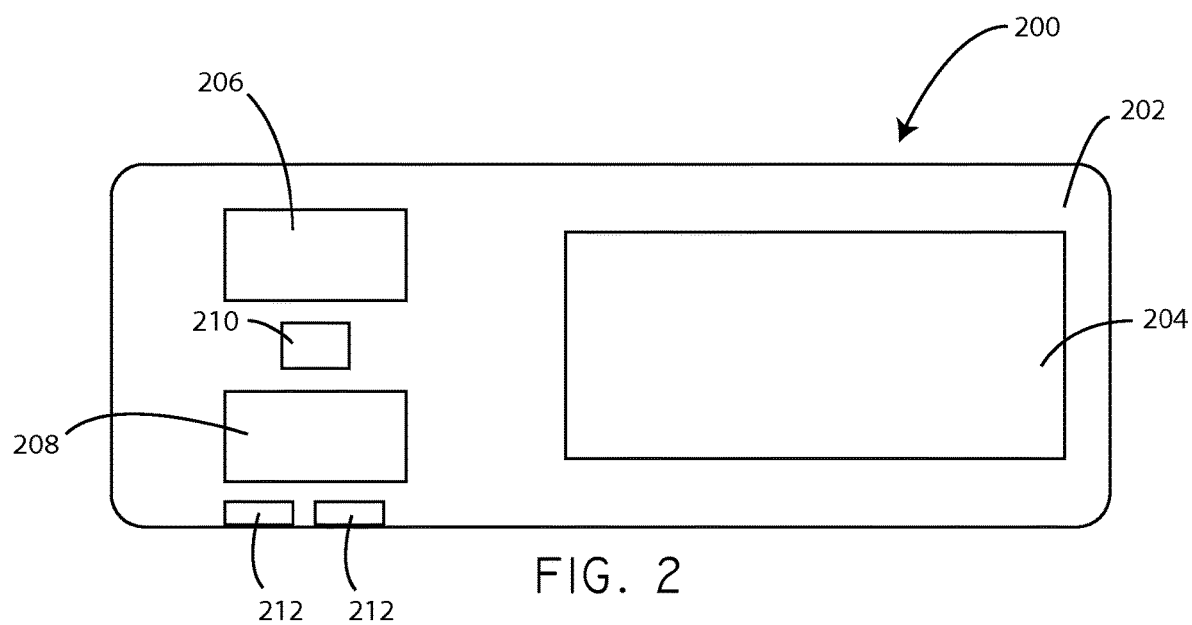
FIG. 2 is a schematic top plan view of a disposable sensor element in accordance with various embodiments herein.

Referring now to FIG. 2, a schematic top view of a disposable sensor element 200 is shown in accordance with various embodiments herein. The sensor element 200 can include a substrate 202, a first measurement zone 204, a second measurement zone 206, a third measurement zone 208, a component 210 to store reference data and electrical contacts 212. The electrical contacts 212 can be used to provide power to components on the disposable sensor element 200 and/or can be used to read data regarding the measurements zones and/or data from the component 210 to store reference data. However, it will be appreciated that in other embodiments there are no external electrical contacts 212 on the disposable sensor element 200.

Figure 3:
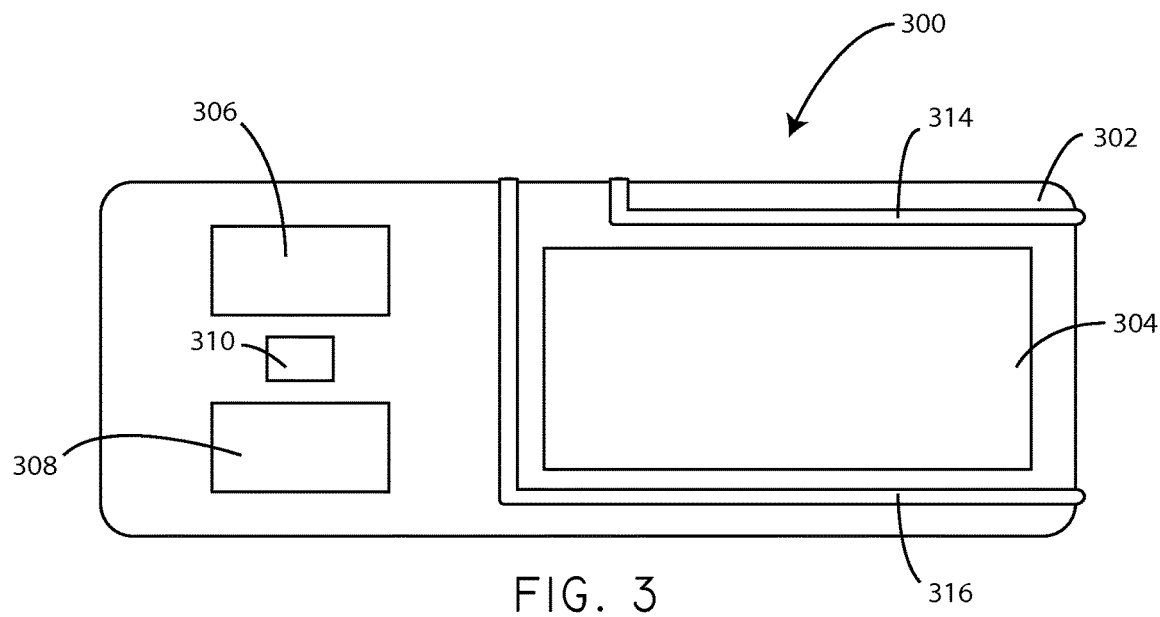
FIG. 3 is a schematic top plan view of a disposable sensor element in accordance with various embodiments herein.
Figure 4:
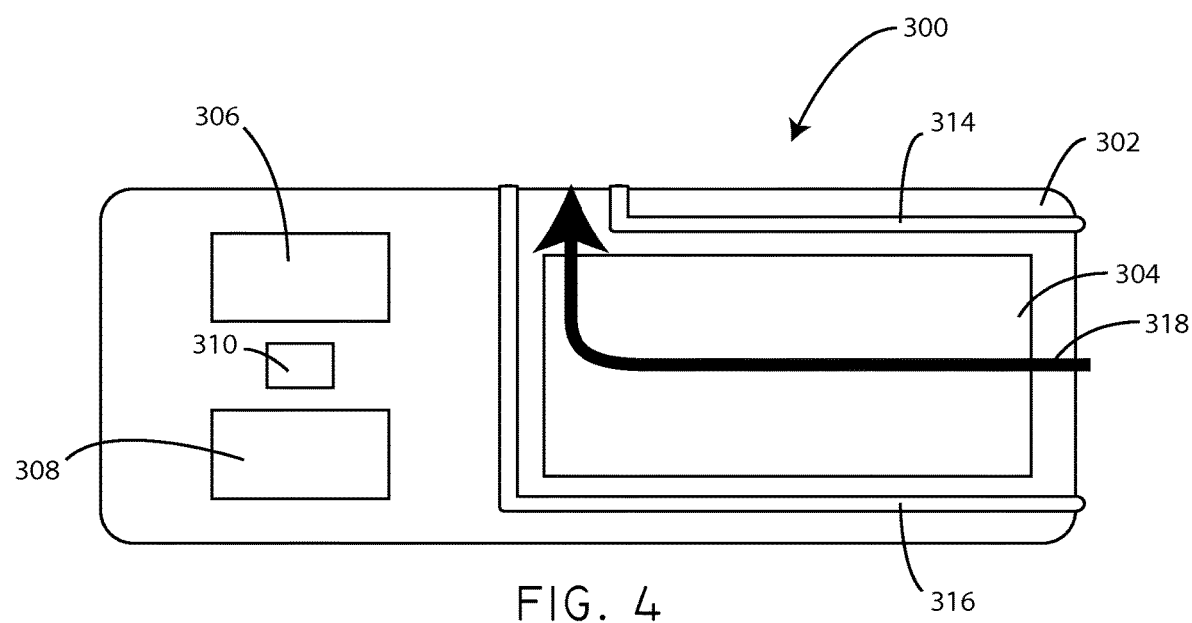
FIG. 4 is a schematic top plan view of a disposable sensor element in accordance with various embodiments herein.

In various embodiments, the disposable sensor elements can include airflow baffles to guide the flow of a gaseous fluid across the surface of the disposable sensor element, such as a breath sample for analysis, an environmental control gas sample, or the like. Referring now to FIG. 3, a schematic top view of a disposable sensor element 300 is shown in accordance with various embodiments herein. The sensor element 300 can include a substrate 302, a first measurement zone 304, a second measurement zone 306, a third measurement zone 308, and a component 310 to store reference data. The sensor element 300 can also include a first baffle 314 and a second baffle 316. The baffles 314, 316 can stick out from the surface of the substrate 302 and engage with another surface that is part of a chamber for holding the disposable sensor element in a sensing system. In this manner, the baffles 314, 316 can help to define and isolate one or more gas flow paths across the surface of the disposable sensor elements. A portion of a first gas flow path 318 is shown in FIG. 4. In some embodiments, a single gas flow path 318 can be defined, at least in part, by the disposable sensor element. In other embodiments, multiple gas flow paths can be defined by the disposable sensor element.

The baffles 314, 316 can include various materials. By way of example, baffles can be formed from polymeric materials including, but not limited to, thermoplastic polymers, thermoset polymers, elastomeric polymers, as well as cellulosic materials, composite materials, metals, ceramics, glasses, and the like.

Figure 5:
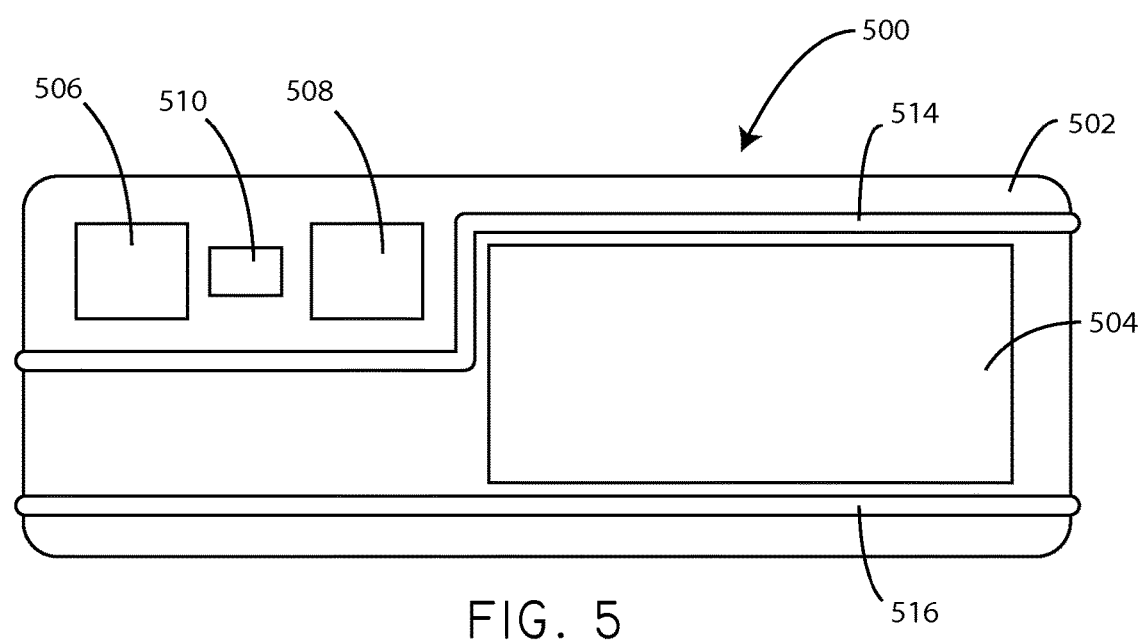
FIG. 5 is a schematic top plan view of a disposable sensor element in accordance with various embodiments herein.

It will be appreciated that the baffles can take on various shapes and configurations. Referring now to FIG. 5, a schematic top view of a disposable sensor element 500 is shown in accordance with various embodiments herein. The sensor element 500 can include a substrate 502, a first measurement zone 504, a second measurement zone 506, a third measurement zone 508, and a component 510 to store reference data. The sensor element 500 can also include a first baffle 514 and a second baffle 516.

Figure 6:
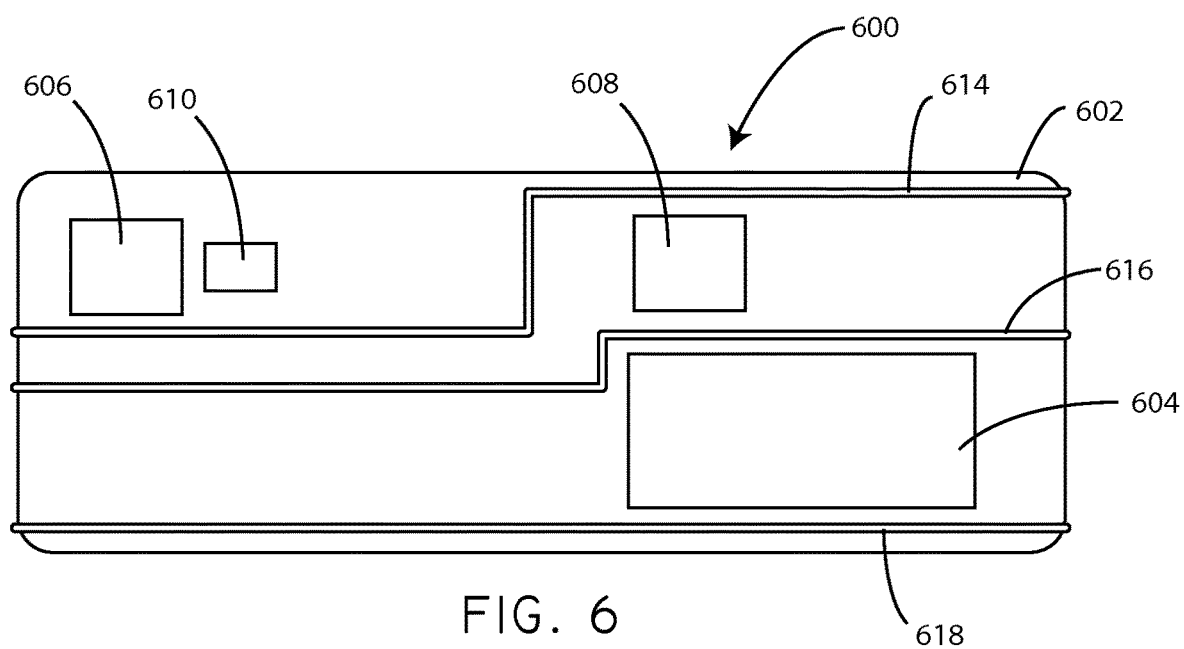
FIG. 6 is a schematic top plan view of a disposable sensor element in accordance with various embodiments herein.

In some embodiments, the disposable sensor element can include multiple gas flow paths. For example, a first gas flow path can serve as a channel for the flow of a gas sample for analysis (such as a breath sample from a patient) and a second gas flow path can serve as a channel for the flow of an environmental control sample (such as a sample of ambient air) to account for background levels of analytes. In embodiments wherein multiple gas flow paths are defined, it will be appreciated that in some cases the gas flow paths result in flow in the same direction and in other cases result in counter-current flow of gases. Referring now to FIG. 6, a schematic top view of a disposable sensor element 600 is shown in accordance with various embodiments herein. The sensor element 600 can include a substrate 602, a first measurement zone 604, a second measurement zone 606, a third measurement zone 608, and a component 610 to store reference data. The sensor element 600 can also include a first baffle 614, a second baffle 616, and a third baffle 618.

Figure 7:
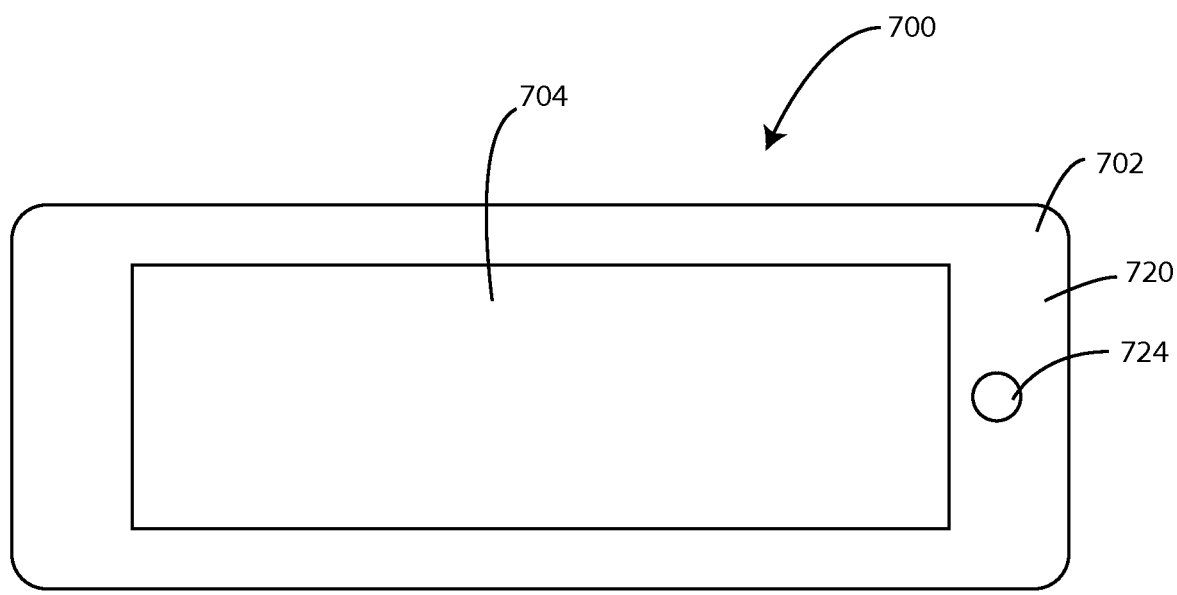
FIG. 7 is a schematic top plan view of a disposable sensor element in accordance with various embodiments herein.

In some embodiments, all of the components of a disposable sensor element can be disposed on the same side of the substrate of the disposable sensor element. In other embodiments the components of the disposable sensor element can be distributed across a first side and an opposing second side. Referring now to FIG. 7, a schematic top view of a disposable sensor element 700 is shown in accordance with various embodiments herein. The sensor element 700 can include a substrate 702 having a first side 720 and can include a first measurement zone 704 disposed on the first side 720.

In some embodiments, the disposable sensor element 700 can optionally include a pressure sensor 724. The pressure sensor 724 can be disposed on the substrate 702. In some embodiments, a pressure sensor 724 can be disposed on both sides of the substrate 702. In some embodiments, the pressure sensor 724 can be disposed within an aperture between the two sides of the substrate 702. The pressure sensor can be used to detect air pressure and changes to the same, such as within the gas flow paths. Various types of pressure sensors can be used including membrane-type sensors including flexion sensors, piezoresistive strain gauge type sensors, capacitive sensors including a diaphragm, electromagnetic sensors, optical pressure sensors, potentiometric pressure sensors and the like.

Figure 8:
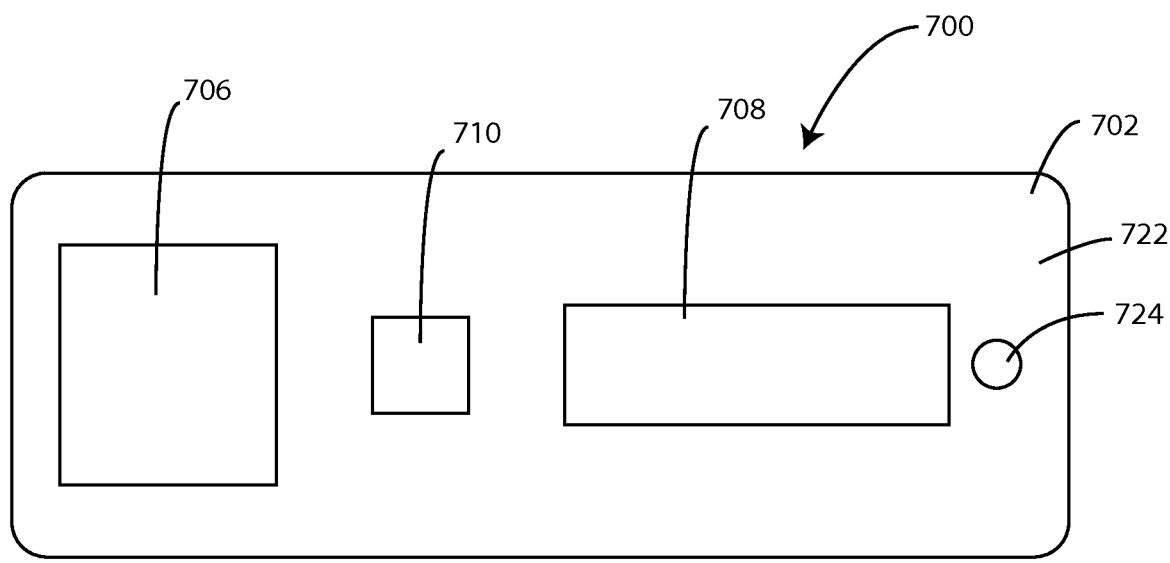
FIG. 8 is a schematic bottom plan view of the disposable sensor element of FIG. 7 in accordance with various embodiments herein.

Referring now to FIG. 8, a schematic bottom view of the disposable sensor element 700 is shown. The sensor element 700 can also include a second side 722 and a second measurement zone 706, a third measurement zone 708, a component 710 to store reference data disposed on the second side 722, and a pressure sensor 724.

Figure 9:
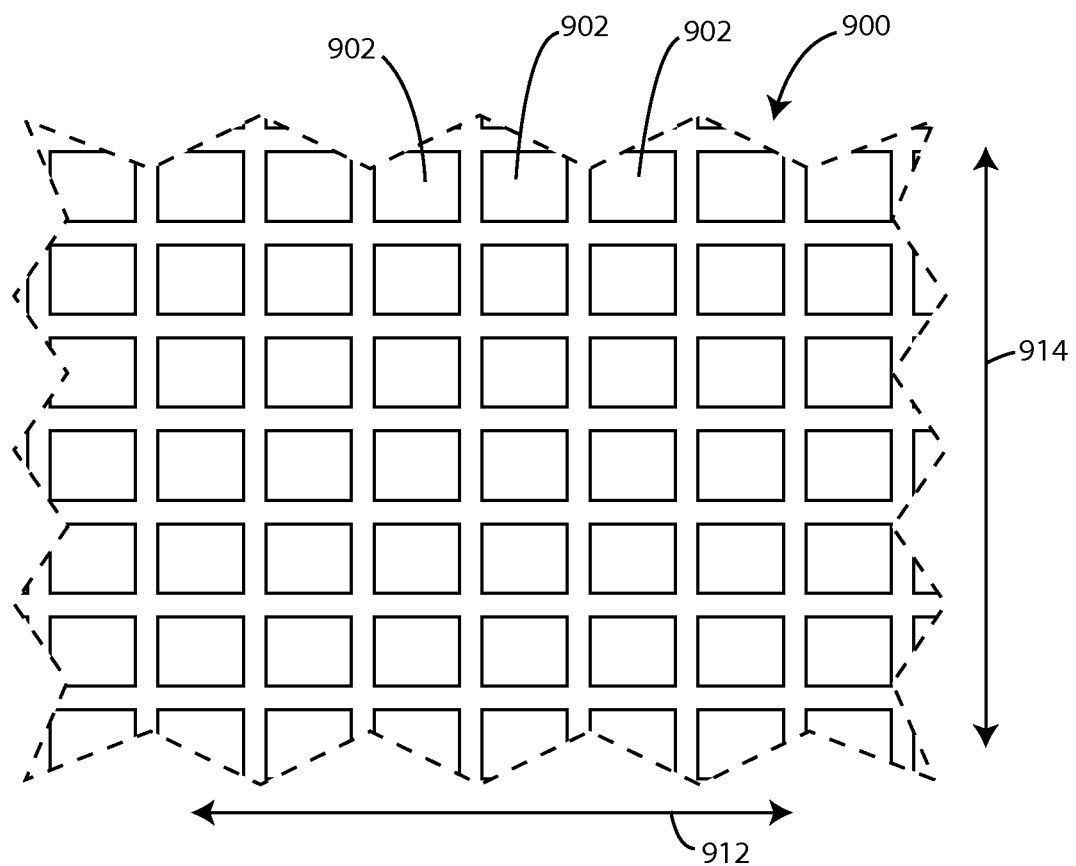
FIG. 9 is a schematic diagram of a portion of a measurement zone in accordance with various embodiments herein.

Referring now to FIG. 9, a schematic diagram of a portion of a measurement zone 900 is shown in accordance with various embodiments herein. A plurality of discrete binding detectors 902 can be disposed within the measurement zone 900. In some embodiments, the discrete binding detectors can be heterogeneous in that they are all different from one another in terms of their binding behavior or specificity with regard to analytes. In some embodiments, some discrete binding detectors can be duplicated for validation purposes, but are otherwise heterogeneous from other discrete binding detectors. While the discrete binding detectors 902 of FIG. 9 are shown as boxes organized into a grid, it will be appreciated that the discrete binding detectors can take on many different shapes (including, but not limited to, various polygons, circles, ovals, irregular shapes, and the like) and, in turn, the groups of discrete binding detectors can be arranged into many different patterns (including, but not limited to, star patterns, zig-zag patterns, radial patterns, symbolic patterns, and the like).

In some embodiments, the order of specific discrete binding detectors 902 across the length 912 and width 914 of the measurement zone can be substantially random. In other embodiments, the order can be specific. For example, in some embodiments, a measurement zone can be ordered so that the specific discrete binding detectors 902 for analytes having a lower molecular weight are located farther away from the incoming gas flow relative to specific discrete binding detectors 902 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete binding detectors.

In some embodiments, a measurement zone can be ordered so that the specific discrete binding detectors 902 for analytes having a lower polarity are located a farther distance from the incoming gas flow and specific discrete binding detectors 902 for analytes having a higher polarity are located closer to the incoming gas flow. Alternately, the discrete binding detectors 902 can be ordered in the opposite manner. In this way, an electric field can be applied near the measurement zones such that the gas samples flow through the electric field and effectively concentrate analytes from the gas samples in the area where the corresponding discrete binding detectors are located.

The number of discrete binding detectors 902 within a particular measurement zone can be from about 1 to about 100,000. In some embodiments, the number of discrete binding detectors 902 can be from about 1 to about 10,000. In some embodiments, the number of discrete binding detectors 902 can be from about 1 to about 1,000. In some embodiments, the number of discrete binding detectors can be from about 2 to about 500. In some embodiments, the number of discrete binding detectors can be from about 10 to about 500. In some embodiments, the number of discrete binding detectors can be from about 50 to about 500. In some embodiments, the number of discrete binding detectors can be from about 1 to about 250.

Each of the discrete binding detectors 902 can include at least a portion of one or more electrical circuits. By way of example, in some embodiments, each of the discrete binding detectors can include one or more passive electrical circuits. The electrical properties of the electrical circuit can change upon binding, such as specific and/or non-specific binding, with a component from a gas sample.

The discrete binding detectors can be functionalized with analyte binding receptors capable of specific binding and/or analyte binding receptors capable of non-specific binding. It will be appreciated that there are various chemistries which can be utilized to facilitate attachment of analyte binding receptors. By way of example, in the context of attachment to a graphene surface, covalent or non-covalent binding approaches can be used. Covalent binding approaches can include the formation of covalent bonds between free radicals or dienophiles of molecules to be attached or intermediates and C=C bonds of graphene layers. Covalent binding approaches can also include the formation of covalent bonds between organic functional groups of molecules to be attached or intermediates and oxygen groups of graphene oxide (a graphene derivative). As just one example, a diazonium salt can be heated producing a highly reactive free radical which attacks the $sp^2$ carbon atoms of graphene forming a covalent bond. The diazonium salt itself can be modified to contain the desired functional group(s) with which the graphene is functionalized or can include linking groups to which other desired functional group(s) can later be attached. Various approaches to the functionalization of graphene are described in Georgakilas et al., *Functionalization of Graphene: Covalent and Non-Covalent Approaches, Derivatives and Applications*, Chemical Reviews, 2012 Nov. 14; 112(11):6156-214; U.S. Publ. Appl. No. 2011/0017587; and U.S. Publ. Appl. No. 2014/0275597, the content of all of which is herein incorporated by reference.

It will be appreciated that there are various structures that can be used as analyte binding receptors. Exemplary structures for binding can include, but are not limited to, antibodies, antibody fragments, nonimmuno-proteins, nucleic acids, other organic receptors, small molecule receptors, inorganic receptors, and the like.

Each particular discrete binding detector can include one or more analyte binding receptors bound thereto. In some embodiments, all of the analyte binding receptors within a particular discrete binding detector can be the same with respect to their analyte binding properties. In other embodiments, at least some of the analyte binding receptors within a particular zone can be different from one another with respect to their analyte binding properties. In some embodiments, each discrete binding detector can be unique. In some embodiments, discrete binding detectors that are unique can be cross-reactive in that they bind to different portions or different configurations of the same chemical compound. In some embodiments, each discrete binding detector can include a single passive sensor circuit. In other embodiments, each discrete binding detector can include multiple passive sensor circuits.

Figure 10:
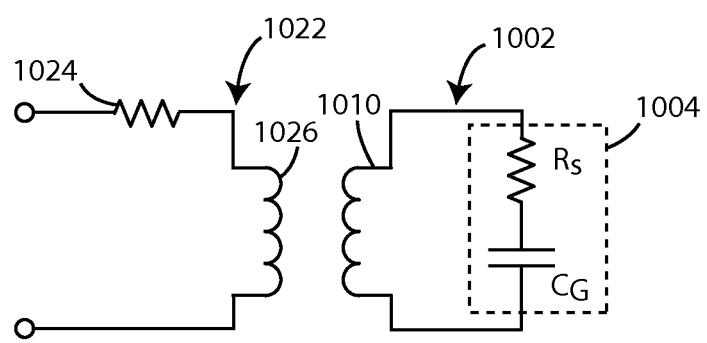
FIG. 10 is a circuit diagram of a passive sensor circuit and a portion of a reading circuit is shown in accordance with various embodiments herein.

Referring now to FIG. 10, a schematic diagram of a passive sensor circuit 1002 and a portion of a reading circuit 1022 is shown in accordance with various aspects herein. In some embodiments, the passive sensor circuit 1002 can include a graphene varactor (variable capacitor) or metal-graphene-oxide capacitor 1004 (wherein RS represents the series resistance and CG represents the varactor capacitor) coupled to an inductor 1010. Graphene varactors can be prepared in various ways and with various geometries. As just one example, in some aspects, a gate electrode can be recessed into an insulator layer. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a material, such as, aluminum oxide, hafnium dioxide, zirconium dioxide, hafnium silicate or zirconium silicate. A graphene layer can be disposed on the dielectric layer. In some aspects, the graphene layer can be a graphene monolayer. Contact electrodes can also be disposed on a surface of the graphene layer. Aspects of exemplary graphene varactors can be found in U.S. Publ. App. No. 2014/0145735, the content of which is herein incorporated by reference.

In various embodiments, the functionalized graphene layer (e.g., functionalized to include analyte binding receptors), which is part of the graphene varactor and thus part of a sensor circuit such as a passive sensor circuit, is exposed to the gas sample flowing over the surface of the measurement zone. The passive sensor circuit 1002 can also include an inductor 1010. In some embodiments, only a single varactor is include with each passive sensor circuit 1002. In other embodiments, multiple varactors are included, such as in parallel, with each passive sensor circuit 1002.

In the passive sensor circuit 1002, the quantum capacitance of the electrical circuit changes upon binding between the analyte binding receptors and a component from a gas sample. The passive sensor circuit 1002 can function as an LRC resonator circuit, wherein the resonant frequency of the LRC resonator circuit changes upon binding with a component from a gas sample.

The reading circuit 1022 can be used to detect the electrical properties of the sensor circuit 1002. By way of example, the reading circuit 1022 can be used to detect the resonant frequency of the LRC resonator circuit and/or changes in the same. In some embodiments, the reading circuit 1022 can include a reading coil having a resistance 1024 and an inductance 1026. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and the value of the phase dip frequency.

Figure 11:
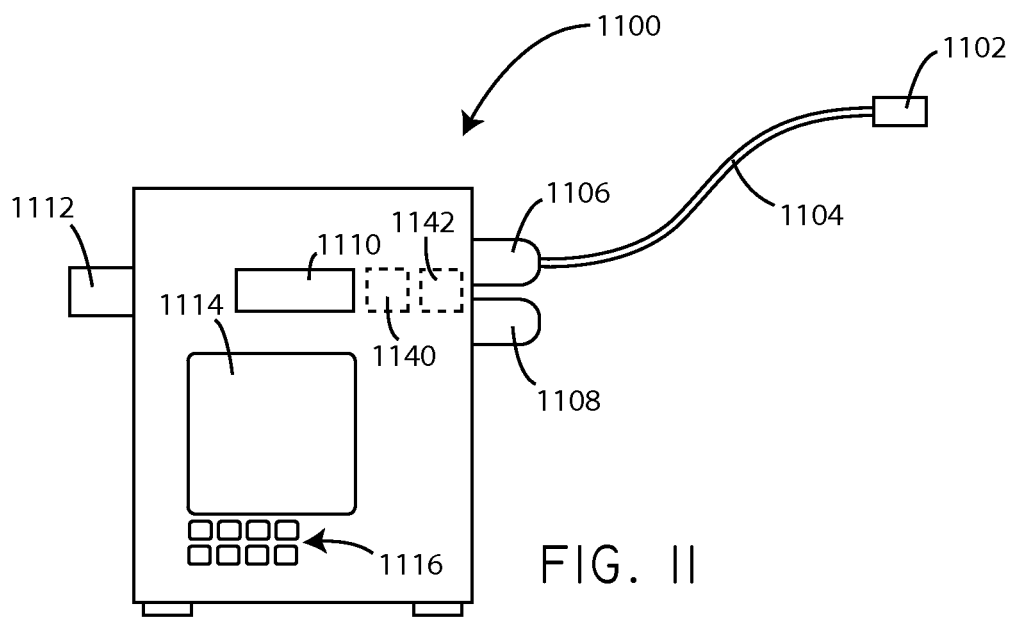
FIG. 11 is a schematic side elevation view of a system for sensing gaseous analytes in accordance with various embodiments herein.

Referring now to FIG. 11, a schematic side elevation view of a system 1100 for sensing gaseous analytes in accordance with various embodiments herein is shown. The system 1100 can include a housing 1118. The system 1100 can include a mouthpiece 1102 into which a subject to be evaluated can blow a breath sample. The gaseous breath sample can pass through an inflow conduit 1104 and pass through an evaluation sample (patient sample) input port 1106. The system 1100 can also include a control sample (environment) input port 1108. The system 1100 can also include a sensor element chamber 1110, into which disposable sensor elements can be placed. The system 1100 can also include a display screen 1114 and a user input device 1116, such as a keyboard. The system can also include a gas outflow port 1112. The system 1100 can also include flow sensors in fluid communication with the gas flow associated with one or more of the evaluation sample input port 1106 and control sample input port 1108. It will be appreciated that many different types of flow sensors can be used. In some embodiments, a hot-wire anemometer can be used to measure the flow of air. In some embodiments, the system can include a $CO_2$ sensor in fluid communication with the gas flow associated with one or more of the evaluation sample input port 1106 and control sample input port 1108.

In various embodiments, the system 1100 can also include other functional components. By way of example, the system 1100 can include a humidity control module 1140 and/or a temperature control module 1142. The humidity control module can be in fluid communication with the gas flow associated with one or more of the evaluation sample input port 1106 and control sample input port 1108 in order to adjust the humidity of one or both gas flow streams in order to make the relative humidity of the two streams substantially the same in order to prevent an adverse impact on the readings obtained by the system. The temperatures control module can be in fluid communication with the gas flow associated with one or more of the evaluation sample input port 1106 and control sample input port 1108 in order to adjust the temperature of one or both gas flow streams in order to make the temperature of the two streams substantially the same in order to prevent an adverse impact on the readings obtained by the system. By way of example, the air flowing into the control sample input port can be brought up to 37 degrees Celsius in order to match the temperature of air coming from a patient. The humidity control module and the temperature control module can be upstream from the input ports, within the input ports, or downstream from the input ports in the housing 1118 of the system 1100. In some embodiments, the humidity control module 1140 and the temperature control module 1142 can be integrated.

In some embodiments (not shown), the control sample input port 1108 of system 1100 can also be connected to a mouthpiece 1102. In some embodiments, the mouthpiece 1102 can include a switching airflow valve such that when the patient is drawing in breath, air flows from the input port 1108 to the mouthpiece, and the system is configured so that this causes ambient air to flow across the appropriate control measurement zone (such as the second measurement zone). Then when the patient exhales, the switching airflow valve can switch so that a breath sample from the patient flows from the mouthpiece 1102 through the inflow conduit 1104 and into the evaluation sample input port 1106 and across the appropriate sample (patient sample) measurement zone (such as the first measurement zone) on the disposable sensor element.

In an embodiment, a method of making a disposable sensor element is included. The method can include depositing one or more measurement zones onto a substrate. The method can further include depositing a plurality of discrete binding detectors within the measurement zones on the substrate. The discrete binding detectors can be as described herein previously. In some embodiments, the method can include functionalizing the discrete binding detectors with analyte binding receptors capable of specific binding and/or analyte binding receptors capable of non-specific binding. The method can further include depositing a component to store reference data onto the substrate. In some embodiments, the measurement zones can all be placed on the same side of the substrate. In other embodiments, the measurement zones can be placed onto different sides of the substrate.

In an embodiment, a method of assaying a gas sample is included. The method can include inserting a disposable sensor element into a testing machine. The disposable sensor element can include a substrate and a first measurement zone comprising a plurality of discrete binding detectors. The first measurement zone can define a portion of a first gas flow path. The disposable sensor element can further include a second measurement zone separate from the first measurement zone. The second measurement zone can also include a plurality of discrete binding detectors. The second measurement zone can be disposed outside of the first gas flow path.

The method can further include prompting a subject to blow air into the testing machine to follow the first gas flow path. In some embodiments, the $CO_2$ content of the air from the subject is monitored and sampling with the disposable sensor element is conducted during the plateau of $CO_2$ content as it is believed that this air originating with the alveoli of the patient which is believed to have the richest content of chemical compounds for analysis, such as volatile organic compounds. In some embodiments, the method can include monitoring the total mass flow of the breath sample and the control (or environmental) air sample using flow sensors. The method can further include interrogating the discrete binding detectors to determine their analyte binding status. The method can further include discarding the disposable sensor element.

Figure 12:
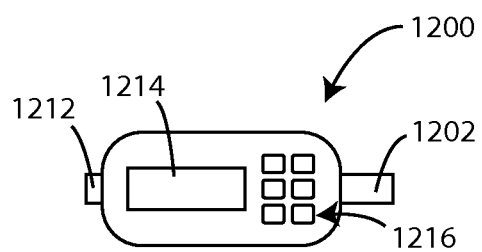
FIG. 12 is a schematic side elevation view of a system for sensing gaseous analytes in accordance with various embodiments herein.

Referring now to FIG. 12, a schematic side elevation view of a system 1200 for sensing gaseous analytes in accordance with various embodiments herein is shown. In this embodiment, the system is in a hand-held format. The system 1200 can include a housing 1218. The system 1200 can include a mouthpiece 1202 into which a subject to be evaluated can blow a breath sample. The system 1200 can also include a display screen 1214 and a user input device 1216, such as a keyboard. The system can also include a gas outflow port 1212. The system can also include various other components such as those described with reference to FIG. 11 above.

Figure 13:
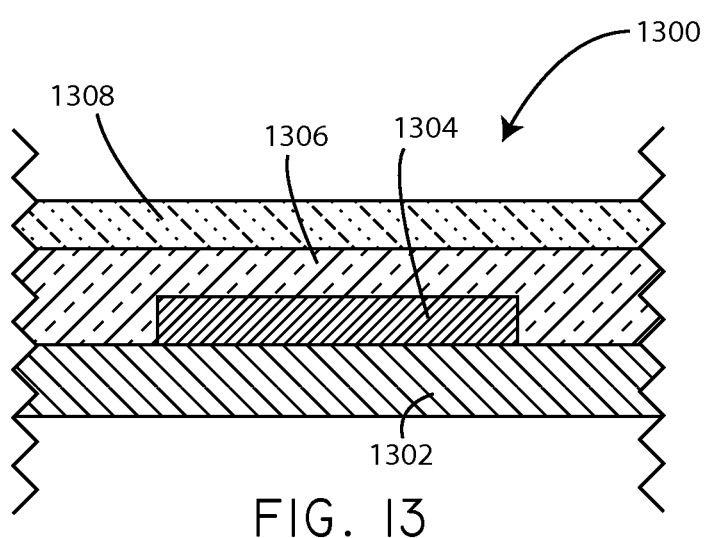
FIG. 13 is a schematic cross-sectional view of a portion of a disposable sensor element in accordance with various embodiments herein.

In some embodiments, one of the measurement zones can be configured to indicate changes (or drift) in the sensor that could occur as a result of aging and exposure to varying conditions (such as heat exposure, light exposure, etc.) during storage and handling prior to use. In some embodiments, the third measurement zone can be configured for this purpose. Referring now to FIG. 13, a schematic cross-sectional view is shown of a portion of a disposable sensor element 1300 in accordance with various embodiments herein. The disposable sensor element 1300 can include a substrate 1302 and a discrete binding detector 1304 disposed thereon that is part of a measurement zone. Optionally, in some embodiments the discrete binding detector 1304 can be encapsulated by an inert material 1306, such as nitrogen gas, or an inert liquid or solid. In this manner, the discrete binding detector 1304 for the third measurement zone can be shielded from contact with gas samples and can therefore be used as a control or reference to specifically control for sensor drift which may occur between the time of manufacturing and the time of use of the disposable sensor element. In some embodiments, such as in the case of the use of an inert gas or liquid, the discrete binding detector can also include a barrier layer 1308, which can be a layer of a polymeric material, a foil, or the like.

In some embodiments, data from such discrete binding detectors can be used to control for sensor drift. For example, a reading can be taken from discrete binding detectors in a third measurement zone (drift control zone or witness zone) at the time of manufacturing the disposable sensor element. The data regarding this zone can be stored in the component to store reference data. Then, another reading can be taken at the time of using the disposable sensor element in an end-use setting. By comparing the data from the two time points, the drift of the sensor can be assessed. In some embodiments, the degree of drift is used when evaluating results from the other measurement zones on the disposable sensor element. In other embodiments, the degree of drift is evaluated against a threshold amount. If the degree of drift exceeds the threshold amount then the system can display an alert to a system user to discard the disposable sensor element.

It will be appreciated that while in many embodiments of disposable sensor elements herein there are two or more measurement zones, in other embodiments there may only be a single measurement zone. Such a single measurement zone can include any of the features previously described herein with respect to measurement zones.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A breath analysis system comprising:
   an evaluation sample input port in fluid communication with an inflow conduit, wherein the inflow conduit is connected to a mouthpiece and is configured to receive an evaluation sample from a patient;
   a control sample input port that is separate from the evaluation sample input port and is configured to receive a control sample from an ambient environment; the control sample input port in fluid communication with the ambient environment; and
   a disposable sensor element comprising:
      a substrate;
      a first measurement zone disposed on the substrate, the first measurement zone comprising
         a plurality of discrete binding detectors comprising graphene varactors; and
      a second measurement zone disposed on the substrate, separate from the first measurement zone, the second measurement zone comprising
         a plurality of discrete binding detectors comprising graphene varactors;
      wherein the inflow conduit, evaluation sample input port, mouthpiece, and first measurement zone define a portion of a first gas flow path;
      wherein the control sample input port and second measurement zone define a portion of a second gas flow path isolated from the first gas flow path such that no portion of the first gas flow path is in fluid communication with any portion of the second gas flow path; and
      wherein the first measurement zone is in fluid communication with the evaluation sample input port for receiving the evaluation sample along the first gas flow path and the second measurement zone is in fluid communication with the control sample input port for receiving the control sample along the second gas flow path.

2. The breath analysis system of claim 1, the substrate having a first side and a second side opposite the first side; the first measurement zone and the second measurement zone both disposed on the first side.

3. The breath analysis system of claim 1, the substrate having a first side and a second side opposite the first side; the first measurement zone disposed on the first side and the second measurement zone disposed on the second side.

4. The breath analysis system of claim 1, the sensor element further comprising a third measurement zone isolated from the first gas flow path and the second gas flow path.

5. The breath analysis system of claim 1, the substrate comprising a material selected from the group consisting of polymers, metals, glasses, ceramics, cellulosic materials and composites.

6. The breath analysis system of claim 5, the discrete binding detectors comprising graphene varactors further comprising a passive electrical circuit.

7. The breath analysis system of claim 1, the discrete binding detectors comprising graphene varactors further comprising at least a portion of an electrical circuit, wherein the electrical properties of the electrical circuit change upon binding of an analyte from a gas sample to the discrete binding detectors.

8. The breath analysis system of claim 1, the discrete binding detectors comprising graphene varactors further comprising a portion of an electrical circuit, wherein the quantum capacitance of the electrical circuit changes upon binding of an analyte from a gas sample to the discrete binding detectors.

9. The breath analysis system of claim 1, the discrete binding detectors comprising graphene varactors further comprising an LRC resonator circuit, wherein the resonant frequency of the LRC resonator circuit changes upon binding of an analyte from a gas sample to the discrete binding detectors.

10. The breath analysis system of claim 1, the discrete binding detectors further comprising a metal-graphene-oxide capacitor.

11. The breath analysis system of claim 1, the discrete binding detectors comprising graphene varactors further functionalized with analyte binding receptors capable of specific binding.

12. The breath analysis system of claim 1, the discrete binding detectors functionalized with analyte binding receptors capable of non-specific binding.

13. The breath analysis system of claim 1, further comprising a baffle mounted on the substrate, the baffle defining a portion of the first gas flow path.

14. The breath analysis system of claim 13, further comprising a second baffle mounted on the substrate, the baffle defining a portion of the second gas flow path.

15. The breath analysis system of claim 11, wherein the discrete binding detectors are ordered so that discrete binding detectors specific for analytes having a lower molecular weight are located farther away from an incoming gas flow than discrete binding detectors specific for analytes having a higher molecular weight.

16. The breath analysis system of claim 11, wherein the discrete binding detectors are ordered so that discrete binding detectors specific for analytes having a lower polarity are located farther away from an incoming gas flow than discrete binding detectors specific for analytes having a higher polarity.

17. The breath analysis system of claim 1, further comprising a storage device, wherein the storage device comprises an electronic data storage device, an optical data storage device, or a printed data storage device.

18. The breath analysis system of claim 1, wherein the evaluation sample from the first gas flow path is a patient breath sample and the control sample from the second gas flow path is an environmental sample.

19. The breath analysis system of claim 1, wherein the control sample input port is connected to the mouthpiece;
wherein the mouthpiece can include a switching airflow valve, the switching airflow valve configured to cause the control sample to flow across the second measurement zone when a patient is drawing in a breath; and
wherein the switching airflow valve is further configured to switch when a patient exhales so that the evaluation sample flows from the mouthpiece through the inflow conduit and into the evaluation sample input port and across the first measurement zone.

* * * * *